(12) United States Patent
Clyde et al.

(10) Patent No.: US 7,097,875 B2
(45) Date of Patent: Aug. 29, 2006

(54) METHODS OF MAKING GAS SENSORS AND SENSORS FORMED THEREFROM

(75) Inventors: Eric P. Clyde, Bay City, MI (US); Richard E. Fouts, Grand Blanc, MI (US); Richard F. Beckmeyer, Davisburg, MI (US); William J. LaBarge, Bay City, MI (US)

(73) Assignee: Delphi Technologies, INC, Troy, MI (US)

( * ) Notice: Subject to any disclaimer, the term of this patent is extended or adjusted under 35 U.S.C. 154(b) by 425 days.

(21) Appl. No.: 10/324,530

(22) Filed: Dec. 19, 2002

(65) Prior Publication Data

US 2004/0117974 A1    Jun. 24, 2004

(51) Int. Cl.
*B05D 5/12* (2006.01)
*B05D 3/02* (2006.01)

(52) U.S. Cl. ............... 427/115; 427/126.3; 427/376.2; 427/383.1

(58) Field of Classification Search ............... 427/115, 427/126.3, 376.2, 383.1; 204/424, 426, 428, 204/429, 431
See application file for complete search history.

(56) References Cited

U.S. PATENT DOCUMENTS

| | | | |
|---|---|---|---|
| 5,593,558 A * | 1/1997 | Sugino et al. ............... 204/429 |
| 6,382,198 B1 | 5/2002 | Smith et al. |
| 6,447,658 B1 * | 9/2002 | Wu et al. ............... 204/424 |
| 6,453,736 B1 | 9/2002 | Gutierrez et al. |
| 6,514,397 B1 | 2/2003 | LaBarge et al. |
| 6,544,467 B1 | 4/2003 | Symons et al. |
| 6,555,159 B1 | 4/2003 | Clyde et al. |
| 6,562,747 B1 | 5/2003 | Symons et al. |
| 6,579,435 B1 | 6/2003 | Wang et al. |
| 6,579,436 B1 | 6/2003 | Wang et al. |
| 6,585,872 B1 | 7/2003 | Donelon et al. |
| 6,616,820 B1 | 9/2003 | Wang et al. |
| 6,630,062 B1 * | 10/2003 | Anderson et al. ........... 204/429 |
| 6,638,405 B1 | 10/2003 | Jain et al. |
| 2001/0054553 A1 * | 12/2001 | Isomura et al. ............. 204/431 |
| 2002/0102349 A1 | 8/2002 | Wu et al. ................ 427/126.1 |
| 2003/0205468 A1 * | 11/2003 | Wu et al. ................... 204/428 |

* cited by examiner

*Primary Examiner*—Brian K. Talbot
(74) *Attorney, Agent, or Firm*—Jimmy L. Funke

(57) ABSTRACT

In one embodiment, a method of making a sensor comprises: forming a slurry comprising a metal oxide, a binder, an acetate, and a reducing material, applying the slurry to at least a portion of a sensing element comprising two electrodes with an electrolyte disposed therebetween, and calcining the slurry to form a protective coating. In one embodiment, a gas sensor, comprises: a sensing element comprising a sensing electrode and a reference electrode having an electrolyte disposed therebetween, and a protective coating disposed over the sensing electrode, wherein the protective coating comprises aluminum oxide, an alpha alumina and about 2 wt % to about 15 wt % solid solution, based upon the total weight of the protective coating.

15 Claims, 2 Drawing Sheets

METHODS OF MAKING GAS SENSORS AND SENSORS FORMED THEREFROM

TECHNICAL FIELD

The present disclosure relates to sensors, and more particularly to gas, e.g., oxygen, sensors.

BACKGROUND

Sensors, in particular gas sensors, have been utilized for many years in several industries (e.g., flues in factories, in furnaces and other enclosures, in exhaust streams such as flues, exhaust conduits, and the like, and in other areas). For example, the automotive industry has used exhaust gas sensors in automotive vehicles to sense the composition of exhaust gases, namely, oxygen. For example, a sensor is used to determine the exhaust gas content for alteration and optimization of the air to fuel ratio for combustion.

One type of sensor uses an ionically conductive solid electrolyte between porous electrodes. For oxygen, solid electrolyte sensors are used to measure oxygen activity differences between an unknown gas sample and a known gas sample. In the use of a sensor for automotive exhaust, the unknown gas is exhaust and the known gas, i.e., reference gas, is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to the partial pressure of a known gas ("reference electrode"). Sensors used in automotive applications typically use a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity at low exhaust temperatures. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where:
E=electromotive force
R=universal gas constant
F=Faraday constant
T=absolute temperature of the gas
$p_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating in fuel-rich or fuel-lean conditions, without quantifying the actual air-to-fuel ratio of the exhaust mixture.

Sensors often comprise a first electrode capable of sensing an unknown gas and a second electrode exposed to a reference gas, with an ionically conductive solid electrolyte disposed therebetween. Materials (contaminants), such as silicon (in forms such as, for example, silica (i.e., silicon dioxide)), lead, and the like, present in the unknown gas (e.g., engine exhaust), can poison or otherwise damage the sensing electrode. In order to prevent poisoning/damage to the sensing electrode, a protective layer can be applied to the sensing electrode. Protective layers can comprise spinels (i.e., magnesium aluminate) or metal oxides that have a high surface area for contaminants (e.g., silicon dioxide). The protective layer traps the contaminants, preventing them from reaching and poisoning the sensing electrode. There remains, however, a need for additional sensors, protective coatings, and methods for producing the sensors and protective coatings that reduce possible poisoning of the electrodes.

SUMMARY

Disclosed herein are gas sensors and methods for making sensors. In one embodiment, a method of making a sensor comprises: forming a slurry comprising a metal oxide, a binder, an acetate, and a reducing material, applying the slurry to at least a portion of a sensing element comprising two electrodes with an electrolyte disposed therebetween, and calcining the slurry to form a protective coating.

In one embodiment, a gas sensor, comprises: a sensing element comprising a sensing electrode and a reference electrode having an electrolyte disposed therebetween, and a protective coating disposed over the sensing electrode, wherein the protective coating comprises aluminum oxide, an alpha alumina and about 2 wt % to about 15 wt % solid solution, based upon the total weight of the protective coating.

The above described and other features are exemplified by the following figures and detailed description.

BRIEF DESCRIPTION OF THE DRAWINGS

Referring now to the figures, wherein like elements are numbered alike in several figures.

DETAILED DESCRIPTION

To inhibit electrode contamination by contaminants such as silica, lead, particulate matter, and the like, a protective coating is preferably formed on at least a portion of gas sensor, i.e., over the sensing electrode. Formation of the protective coating can comprise applying a stabilized metal oxide coating to the sensor, for example, by dipping the electrode into a slurry comprising a metal oxide (e.g., alumina) that has been stabilized by a metal such as lanthanum, barium, or the like. Since it has been discovered that, in a slurry, the stabilizer can dissociate with the metal oxide, e.g., leach out of the metal oxide, such that the resultant protective coating will not be stabilized or will not be sufficiently stabilized and such that the slurry will have a very limited life (typically less than or equal to about 6 days), a slurry stabilizer is also preferably employed. Consequently, in one embodiment, the method for forming a protective coating on the electrode comprises contacting at least a portion of a sensor element with a stabilized metal oxide (e.g., lanthanum stabilized alumina) slurry comprising a slurry stabilizer (e.g., an acetate salt). The slurry described herein provides a shelf-stable slurry with appropriate casting rheology for use in making gas sensors.

Although described in connection with an oxygen sensor, it is to be understood that the protective coating can be employed with any type of sensor, such as nitrogen oxide sensor, hydrogen sensor, hydrocarbon sensor, and the like. Although described in connection with a planar sensor and a conical sensor, it is to be understood that the protective coating can be employed with any type of sensor, such as a wide-range, switch-type, and the like.

Figure 1:
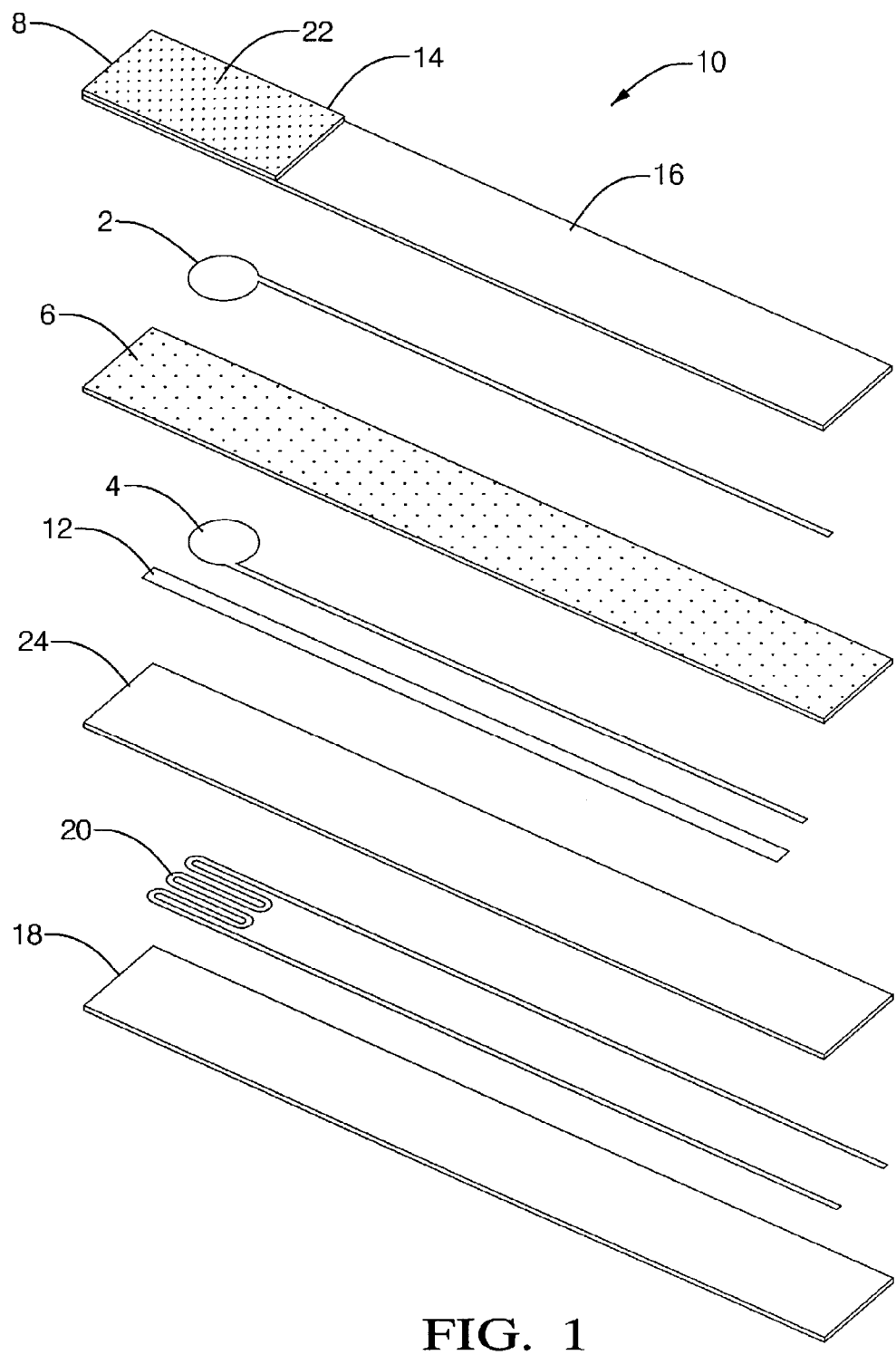
FIG. 1 is an expanded view of one embodiment of a planar oxygen sensor element.

Referring to FIG. 1, an exemplary planar gas sensor element 10 is illustrated. The sensing (i.e., first, exhaust gas or outer) electrode 2 and the reference gas (i.e., second or inner) electrode 4 are disposed on opposite sides of, and adjacent to, an electrolyte layer 6 creating an electrochemical cell (2/6/4). On the side of the sensing electrode 2, opposite solid electrolyte 6, is a protective layer 8 that enables fluid communication between the sensing electrode 2 and the exhaust gas. This protective layer may optionally comprise a porous portion 14 disposed adjacent to the sensing electrode 2 and a solid portion 16. Disposed over at least a portion of the protective layer 8, adjacent to the sensing electrode 2 is a protective coating 22.

Meanwhile, disposed on the side of the reference electrode 4, opposite solid electrolyte 6, can be an optional reference gas channel 12, which is in fluid communication with the reference electrode 4 and optionally with the ambient atmosphere and/or the exhaust gas. Disposed on a side of the reference gas channel 12, opposite the reference electrode 4, may optionally be a heater 20 for maintaining sensor element 10 at a desired operating temperature. Disposed between the reference gas channel 12 and the heater 20, as well as on a side of the heater opposite the reference gas channel 12, can be one or more insulating layers 10, 18.

In addition to the above sensor components, other sensor components can be employed, including but not limited to, lead gettering layer(s), leads, contact pads, ground plane layers(s), support layer(s), additional electrochemical cell(s), and the like. The leads, which supply current to the heater and electrodes, are often formed on the same layers as the heater and the electrodes to which they are in electrical communication and extend from the heater/electrode to the terminal end of the gas sensor where they are in electrical communication with the corresponding via (not shown) and appropriate contact pads (not shown).

The electrolyte 6, which may be a solid electrolyte, can be formed of a material that is capable of permitting the electrochemical transfer of oxygen ions while inhibiting the passage of exhaust gases. Possible electrolyte materials include zirconium oxide (zirconia), cerium oxide (ceria), calcium oxide, yttrium oxide (yttria), lanthanum oxide, magnesium oxide, and the like, as well as combinations comprising at least one of the foregoing electrolyte materials, such as yttria doped zirconia, and the like.

Disposed adjacent to electrolyte 6 are electrodes 2, 4. The sensing electrode 2, which is exposed to the exhaust gas during operation, preferably has a porosity sufficient to permit diffusion to oxygen molecules therethrough. Similarly, the reference electrode 4, which can be exposed to a reference gas such as oxygen, air, or the like, during operation, preferably has a porosity sufficient to permit diffusion to oxygen molecules therethrough. These electrodes can comprise a metal capable of ionizing oxygen, including, but not limited to, platinum, palladium, gold, rhodium, iridium and ruthenium; and metal oxides, such as zirconia, yttria, ceria, calcium oxide, aluminum oxide (alumina), and the like; as well as combinations comprising at least one of the foregoing metals and metal oxides. Other additives such as zirconia may be added to impart beneficial properties such as inhibiting sintering of the platinum to maintain porosity.

Heater 20 can be employed to maintain the sensor element at the desired operating temperature. Heater 20 can be a heater capable of maintaining the end of the sensor adjacent to the electrodes at a sufficient temperature to facilitate the various electrochemical reactions therein. Heater 20, which can comprise, for example, platinum, aluminum, palladium, and the like, as well as mixtures, oxides, and alloys comprising at least one of the foregoing metals can be screen printed or otherwise disposed onto a substrate to a thickness of about 5 micrometers to about 50 micrometers.

Optional insulating layers 10, 18 provide structural integrity (e.g., protect various portions of the sensor element from abrasion and/or vibration, and the like, and provide physical strength to the sensor), and physically separate and electrically isolate various components. The insulating layer(s) can each be up to about 200 micrometers thick or so, with a thickness of about 50 micrometers to about 200 micrometers preferred. The insulating layers 10, 18 can comprise a dielectric material such as alumina, and the like.

In a planar sensor, the sensor element components, e.g., electrodes 2, 4, electrolyte 6, insulating layer(s) 10, 18, heater 20, protective layers 8 and the like, are formed using techniques such as tape casting methods, sputtering, punching and placing, spraying (e.g., electrostatically spraying, slurry spraying, plasma spraying, and the like), dipping, painting, and the like, as well as combinations comprising at least one of the foregoing techniques. The component layers are then stacked and aligned in accordance with the particular type of sensor. Although the layers may be separately calcined, they are preferably co-fired. Optionally, the aligned layers can be heat treated to formed laminated stacks often referred to as "tiles" that contain multiple sensor elements.

Figure 2:
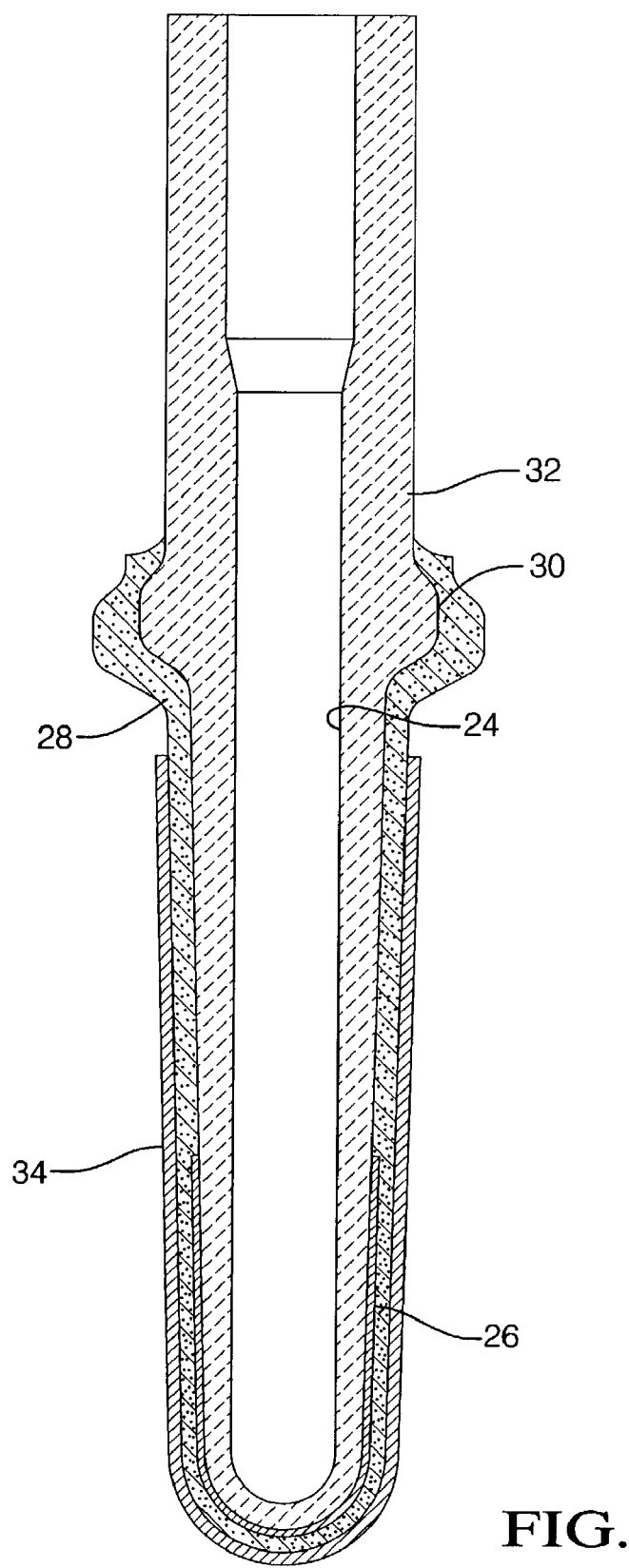
FIG. 2 is a cross-sectional schematic of one embodiment of a conical oxygen sensor.

An alternative sensor design can include a conical sensor as is illustrated in FIG. 2. The conical sensor typically comprises a conically shaped electrolyte 32 with an inner electrode 24 disposed on the inner surface of the electrolyte 32 and an outer electrode 26 disposed on outer surface of the electrolyte 32. An optional protective layer 28, which is disposed over the outer electrode 26, optionally extends over the hips 30. Disposed over the sensing electrode 26, and over optional protective layer 28 is protective coating 34. The sensor component materials, as indicated above for the planar sensor, can also be utilized with the conical sensor.

Forming the sensor elements comprises forming a slurry that will be applied to the sensor element to form the protective coating (22, 34). Forming the slurry comprises combining a metal oxide with a solvent, an acetate salt, and optionally a reducing material. Optionally, the pH is adjusted. Once formed, the slurry can be disposed on at least a portion of the sensing element. The sensing element can be fired prior to the application of the slurry or co-fired with the slurry. The coated sensor element can then be heated to remove volatiles and the reducing material, if any.

The metal oxide employed in the slurry preferably comprises a high surface area (e.g., greater than or equal to about 100 m$^2$/g (square meters per gram)) material. Possible materials such as high temperature materials, including aluminum oxides (such as theta-alumina ($\theta$—Al$_2$O$_3$), gamma-alumina ($\gamma$—Al$_2$O$_3$), delta-alumina ($\delta$—Al$_2$O$_3$), barium stabilized aluminum oxide, lanthanum stabilized aluminum oxide, barium-lanthanum stabilized aluminum oxide, strontium stabilized aluminum oxide, and the like), hexaaluminates (e.g., barium hexaaluminate (BaAl$_{12}$O$_{19}$), strontium hexaaluminate (SrAl$_{12}$O$_{19}$) and magnesium hexaaluminate (MgAl$_{12}$O$_{19}$), lanthanum hexaaluminate (LaAl$_{11}$O$_{18}$) and cerium hexaaluminate (CeAl$_{11}$O$_{18}$), bariumlanthanum hexaaluminate (Ba$_{0.5}$La$_{0.7}$Al$_{11}$O$_{18}$) and strontium-lanthanum hexaaluminate (Sr$_{0.8}$La$_{0.2}$Al$_{11}$O$_{18}$)), titanium oxide, zirconium oxide, and the like, as well as combinations comprising at least one of the foregoing materials. Preferably, the alumina has an average particle size, measured along the major axis (i.e., the longest axis) of greater than or equal to about 0.2 micrometers in diameter, with about 2 micrometers to about 5 micrometers in diameter preferred. The metal oxide can comprise a combination of metal oxides, theta-alumina, gamma-alumina, and/or delta-alumina combined with alpha alumina ($\alpha$—Al$_2$O$_3$). The alpha alumina preferably has a particle diameter, measured along the major axis, of less than or equal to about 10 micrometers, with less than or equal to about 0.5 micrometers preferred.

The slurry also preferably comprises a binder compatible with the metal oxide. The binder can be a metal nitrate, for example, such as aluminum nitrate (Al(NO$_3$)$_3$). The slurry can comprise a sufficient amount of the high surface area alumina, alpha alumina, and alumina such that the calcined protective coating comprises about 45 weight percent (wt %) to about 75 wt % of the high surface area alumina, about 25 wt % to about 55 wt % of alpha alumina, and about 2 wt % to about 10 wt % of metal oxide formed from the binder (e.g., alumina formed from alumina nitrate).

Preferentially, the slurry can be stirred prior to being milled (e.g., using a vibro-energy grinding mill or the like) for about 2 hours, or so, to break down the aggregates of the high surface area aluminum oxide. During milling, the size of the high surface area aluminum oxide (e.g., $\theta$—Al$_2$O$_3$) aggregates (d$_{50}$) decrease to less than about 5 micrometers. After milling the slurry, additional coarse aluminum oxide (e.g., the high surface area aluminum oxide) with particle size of about 10 micrometers to about 50 micrometers can be added to the milled slurry. The ratio of milled solids to un-milled solids is preferably about 3:1. The slurry containing un-milled solids is preferably mixed, e.g., for about 2 hours or so.

Also included in the slurry, added concurrently with the metal oxide(s) and solvent, or after these components have been mixed, is an acetate. The slurry comprises a soluble zirconium salt and a soluble aluminum salt, and a highly dispersed reducing agent (e.g., carbon) with at least one of the salts being acetate (e.g., zirconium acetate, ammonium acetate, aluminum acetate, titanium acetate, and the like), to form an aluminum-zirconium solid solution, aluminum-titanium solid solution, a titanium-zirconium solid solution, a titanium-aluminum-zirconium solid solution, or the like. For example, zirconium acetate and aluminum nitrate can be the soluble salts or zirconium nitrate and aluminum acetate can be the soluble salts. The acetate salt can comprise, for example, zirconium acetate (Zr(OH)$_2$(C$_2$H$_3$O$_2$)$_2$), aluminum diacetate hydroxide (Al(C$_2$H$_3$O$_2$)$_2$OH), dihydroxyaluminum acetate (Al(C$_2$H$_3$O$_2$)(OH)$_2$), ammonium acetate (NH$_4$(C$_2$H$_3$O$_2$)), and the like, and combinations comprising one or more of the foregoing acetate salts. The acetate can be included in the slurry in an amount that when the coating is calcined, about 2 wt % to about 15 wt % a solid solution is present in the coating, based upon the total weight of the coating. Within this range, the amount of solid solution is preferably greater than or equal to about 3 wt %, with greater than or equal to about 5 wt % more preferred. Also preferred within this range is an amount of solid solution of less than or equal to about 10 wt % with less than or equal to about 8 wt % more preferred. For example, the solid solution can comprise about 2 wt % to about 8 wt % zirconium, about 1 wt % to about 7 wt % aluminum, and up to about 5 wt % titanium, with about 3 wt % to about 6 wt % zirconium, and about 2 wt % to about 5 wt % aluminum or about 1 wt % to about 5 wt % titanium preferred.

Preferably, the slurry also comprises an optional reducing material such as amorphous carbon (e.g., carbon black, other carbonaceous materials, and the like), polymers which will decompose to non-graphitic carbon, or other appropriate substitute. As used herein, a "reducing material" means a material that will reduce surface tension, enhancing the slurry dispersion and fluidity until the coating is heated to a desired point, thus eliminating slumping during drying, leaving a defect free surface coating e.g. eliminating cracks and pits. In addition, the carbon provides a template for the structure of the aluminum-zirconium solid solution. The reducing agent can be present in an amount of about 1 wt % to about 15 wt %, base upon the total weight of the solids of the slurry (excluding the reducing material). Preferably, the reducing material is present in an amount of greater than or equal to about 3 wt %, with greater than or equal to about 5 wt % more preferred. The reducing template material can also be present in an amount of less than or equal to about 10 wt %. Preferably, the soluble salts are adsorbed on the amorphous carbon. When the carbon is calcined, highly active aluminum-zirconium solid solutions is left dispersed throughout the poison protective layer.

The acetate salts and reducing agent/template/rheology adjuster can be mixed into the slurry by any method. For example, they can be mixed into the slurry by rolling (e.g., slow rolling at less than or equal to about 50 rpm) on, for example, a ball mill roller to form a final slurry. The final slurry can be allowed to stabilize, e.g., for up to about 4 hours or longer.

Preferably, the pH of the final slurry is controlled to attain and maintain a desired viscosity. The pH of the slurry is related to the viscosity of the slurry, such that, at higher pHs (e.g., 3.5 to 5.2), minor changes in the pH dramatically affect the viscosity (e.g., a change of 1.0 in pH can result in a greater than an 800 centipoises change in viscosity). Consequently, a slurry pH of less than or equal to about 5 is preferably employed, with a pH of about 2.5 to about 4.8 preferred. Within this range, a pH of less than or equal to about 4.5 is preferred, with less than or equal to about 4.3, more preferred. Also preferred in this range is a slurry pH of greater than or equal to about 3.0, with a slurry pH of greater than or equal to about 3.8 more preferred. The pH can be adjusted by adding acetate that does not adversely affect the metal oxide(s), binder, acetate, and reducing material, e.g., ammonium acetate (NH$_4$(C$_2$H$_3$O$_2$)) to the slurry. Preferably, the LV viscosity of this slurry, at a spindle speed of about 6.0 revolutions per minute (rpm), with spindle number 2, is greater about 1,900 centipoises (cps) to about 2,450 cps.

Once the pH has been adjusted, if necessary, the slurry can be applied as a protective coating to at least a portion of the sensing element. For example, the sensing element can be dipped into the slurry, which is preferably stirred at a constant speed and then withdrawn from the slurry. Alternatively, the coating can be applied to the sensing element by a variety of techniques, including immersion, screen printing, stenciling, spraying, painting, and the like. The amount of coating deposited onto the sensing element depends upon the physical and chemical properties of the slurry, such as viscosity and pH, as well as the withdrawal rate. For example, when a conical oxygen sensor element was dipped into slurry having a viscosity of 2,150 cps and a pH of 4.3, about 150 milligrams (mg) to about 350 mg of protective coating adhered to the element (via wet pickup) by manipulating the withdrawal rate. The protective coating created was uniform and crack-free. About 200 milligrams to about 300 milligrams of wet pickup (or about 12 milligrams to about 190 milligrams of calcined pickup) is preferred.

Following coating, the sensing element is optionally dried at temperatures up to about 100° C. Next, the element can be calcined at a temperature sufficient to burn off the reducing material, such as about 550° C. to about 800° C., with about 120° C. to about 650° C. preferred, for up to about 2 hours or so, prior to assembly into the sensor. During calcination, the oven ramp rate preferably does not exceed about 10° C./minute, with about 5° C./minute preferred, at temperatures below about 400° C., in order to produce crack-free coatings.

The desired thickness of the protective coating is based upon the ability to filter out poisoning particulates while allowing passage of the exhaust gases to be sensed. Although a multi-layered coating can be employed, the protective coating is preferably a single layer having an overall thickness of about 10 micrometers to about 300 micrometers. The coating thickness can be less than or equal to about 200 micrometers. Preferably, a thickness of greater than or equal to about 90 micrometers is employed.

EXAMPLES

Example I: A thixotropic slurry was prepared by adding 4,800 grams alpha aluminum oxide, 4,800 grams barium stabilized gamma-delta aluminum oxide doped with 3 wt % barium (specifically CONDEA Vista Puralox® SCFA 140 B3), 1,120 grams zirconium acetate (18% solids when calcined), 1,470 grams aluminum nitrate crystals, and 10,200 grams distilled water. The mixture was high shear mixed for 20 minutes. The mixed slurry was then attrition milled for 2 hours. About 2,500 grams of un-milled 3 wt % barium stabilized gamma-delta aluminum oxide and about 490 grams amorphous carbon was added to the slurry. The mixture was high shear mixed for about 30 minutes.

The coating was applied to a sensor by dipping the sensor into the slurry using an automated dipping machine. The slurry viscosity drops as the shear rate increases. Sensors were dipped into the slurry and withdrawn, leaving a deposit of slurry on the parts of 180 to 300 milligrams (mg). If the "pickup" was less than 90 mg calcined, the rate of withdraw was decreased. If the "pickup" was greater than about 150 mg calcined, rate of withdraw was increased. The sensor was then dried for 10 minutes at about 80° C. and then calcined at a temperature of at least 600° C. for 2 hours.

Example II: A thixotropic slurry was prepared by adding 4,800 grams lanthanum hexaaluminate, 4,800 grams barium hexaaluminate, 1,120 grams zirconium acetate, 1,470 grams aluminum nitrate, 240 grams ammonium acetate, and 10,800 grams distilled water. The mixture was high shear mixed for 20 minutes. The mixed slurry was attrition milled for 2 hours. About 1,200 grams of un-milled barium hexaaluminate and about 760 grams amorphous carbon was added to the slurry. The mixture was high shear mixed for about 30 minutes.

The coating was applied to a sensor by dipping the sensor into the slurry using an automated dipping machine. The sensor was then dried for 10 minutes at 80° C., and then calcined at a temperature of at least 600° C. for 2 hours. Preferably, the sensor is dried and calcined with microwaves.

Without being held to theory, it is believed that the nitrate ions in the slurry (i.e., from the binder) impart a high surface tension to the slurry thus affecting the ability of the slurry to coat the sensor element. Further, because the nitrate ions, in the absence of acetate, do not penetrate the carbon (i.e., the reducing material) and do not deposit uniformly on the carbon surface, the carbon (i.e., reducing material) does not disperse well in the slurry. While surfactants can be used to modify carbon surfaces, the large quantity of nitrate ion in the slurry limits the use of most organic surfactants. Wetting agents such as alcohols cannot be used because they disrupt the formation of strong ceramic bonds. Thus, slurries comprising both nitrate ions and carbon can present difficulties in coating of sensor elements.

It has been unexpectedly found herein that the addition of acetate salts to a slurry (i.e., an aluminum oxide slurry) improves the properties (including the shelf-life) of the slurry. Without being held to theory, it is believed that the acetate salt modifies the carbon surface (i.e., reducing material surface) by wetting and filling the porous carbon particle. The interaction of the acetate salt with the carbon reduces carbon flocculation. It is believed that deflocculated carbon particles fill the voids between the aluminum oxide aggregates in the slurry. Such void filling allows better packing and allows reduction in the water content of the slurry. Reduced water content improves the casting rheology and thus reduces slumping during "casting of the coating". Reduced slumping results in fewer cracks and pits in the coatings formed.

The slurry produced by the disclosed methods has improved steady-shear viscosity and dynamic elastic modulus over previous slurries. In addition, the slurries exhibit good dispersion and fluidity at high solids loading. The slurries produced have improved shelf-life as compared to other alumina slurries. A slurry containing aluminum oxides, aluminum nitrate and carbon has a shelf life less than 7 days. The viscosity increases rapidly over those 7 days until wet weight pickups are too heavy. A slurry containing acetates, particularly zirconium acetate, aluminum oxides, aluminum nitrates and carbon has a shelf life greater than 12 months. The viscosity increases less than 25% over a 12 month period.

In addition, the inclusion of an acetate salt in the base slurry results in improvements in the calcined coating. The chemically reducing nature of carbon can facilitate the decomposition of the nitrates upon calcination. When the slurry comprises zirconium acetate (i.e., an acetate salt), calcination results in the formation of high surface area (e.g., with surface area equal to 125 square meters per gram ($m^2$/g)) with varied distribution of agglomerates with primary particle size about 7 nanometers (nm). The aluminum-zirconium solid solution is about 4 wt % of the washcoat weight. (i.e., about 1 wt % to about 4 wt % aluminum-zirconium solid solution, based upon the total weight of the protective coating). These aluminum-zirconium oxide particles can fill the voids left by carbon (i.e., reducing material) burnoff. The size of the aluminum-zirconium oxide particles formed in this manner can be about 2 nanometers or less. The surface area and micro pore volume of aluminum-zirconium oxide particles formed during the calcinations process can reach surface area values as high as about 180 $m^2/g$ (about 0.18 $cm^3/g$ (cubic centimeters per gram)) or greater. The presence of aluminum-zirconium oxide inhibits stabilized aluminum oxide grain growth caused by high temperatures while in use. Reduced grain growth limits volume shrinkage of the coating, thus reducing coating cracking. When there are fewer cracks in the coating, poisoning through the cracks is reduced.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of making a sensor comprising an electrode and a protective coating applied to the electrode, said method comprising:
   forming a slurry comprising metal oxide particles dispersed in a solvent, said slurry further comprising a binder, an acetate salt, and a carbonaceous material;
   applying the slurry to the electrode to form a layer thereon; and
   calcining the layer at a temperature and for a time effective to burn off the carbonaceous material and bond the metal oxide particles to form the protective coating.

2. The method of claim 1, wherein the metal oxide particles comprises an aluminum oxide particles having a surface area of greater than or equal to about 100 $m^2/g$, and composed of an alumina selected from the group consisting of theta-alumina, gamma-alumina, and delta-alumina.

3. The method of claim 2, wherein the calcined protective coating comprises about 45 wt % to about 49 wt % aluminum oxide particles, about 45 wt % to about 49 wt % of alpha alumina particles, and about 2 wt % to about 10 wt % a binder metal oxide formed from the binder, based upon the total weight of the calcined protective coating.

4. The method of claim 1, wherein the binder comprises aluminum nitrate.

5. The method of claim 1, wherein the acetate salt is selected from the group consisting of zirconium acetate, ammonium acetate, aluminum acetate, titanium acetate, and combinations comprising one or more of the foregoing acetates.

6. The method of claim 1, wherein the acetate salt comprises zirconium acetate.

7. The method of claim 1, further comprising co-firing the sensing element and the layer.

8. The method of claim 1, wherein the metal oxide particles are aluminum oxide particles, and the acetate salt comprises zirconium or titanium in an amount effective to form a solid solution at the surface of the aluminum oxide particles during calcining.

9. The method of claim 8, wherein the solid solution comprises about 2 wt % to about 15 wt %, based upon a total weight of the protective coating.

10. The method of claim 9, wherein the the solid solution comprises about 3 wt % to about 10 wt %, based upon a total weight of the protective coating.

11. The method of claim 10, wherein the solid solution comprises about 5 wt % to about 8 wt %, based upon a total weight of the protective coating.

12. The method of claim 1, wherein the slurry has a pH of about 2.5 to about 4.8.

13. The method of claim 12, wherein the pH is about 3.0 to about 4.5.

14. The method of claim 13, wherein the pH is about 3.8 to about 4.3.

15. The method of claim 14, wherein the protective coating has a thickness of about 12 micrometers to about 200 micrometers.

* * * * *